(12) United States Patent
Tsuyuki

(10) Patent No.: US 7,079,618 B2
(45) Date of Patent: Jul. 18, 2006

(54) X-RAY COMPUTED TOMOGRAPHIC APPARATUS

(75) Inventor: Masaharu Tsuyuki, Nasu-gun (JP)

(73) Assignees: Kabushiki Kaisha Toshiba, Tokyo (JP); Toshiba Medical Systems Corporation, Otawara (JP)

( * ) Notice: Subject to any disclaimer, the term of this patent is extended or adjusted under 35 U.S.C. 154(b) by 11 days.

(21) Appl. No.: 10/798,478

(22) Filed: Mar. 12, 2004

(65) Prior Publication Data

US 2004/0179644 A1    Sep. 16, 2004

(30) Foreign Application Priority Data

Mar. 14, 2003  (JP)  ............................ 2003-070938

(51) Int. Cl.
*G01N 23/00* (2006.01)

(52) U.S. Cl. ............................ 378/8; 378/15

(58) Field of Classification Search ............ 378/8, 378/15, 901, 4, 16
See application file for complete search history.

(56) References Cited

U.S. PATENT DOCUMENTS

| | | | |
|---|---|---|---|
| 6,639,965 B1 * | 10/2003 | Hsieh et al. ................ | 378/8 |
| 6,763,082 B1 * | 7/2004 | Ozaki ........................... | 378/8 |
| 2002/0136350 A1 | 9/2002 | Pan et al. ...................... | 378/8 |
| 2003/0161435 A1 | 8/2003 | Ozaki ........................... | 378/4 |

FOREIGN PATENT DOCUMENTS

| | | |
|---|---|---|
| EP | 0 983 747 | 3/2000 |
| EP | 1 090 586 | 4/2001 |
| JP | 2000-342577 | 12/2000 |

OTHER PUBLICATIONS

M. Kachelriess, et al., Med. Phys., vol. 27, No. 8, XP-001108143, pp. 1881-1902, "ECG-Correlated Image Reconstruction From Subsecond Multi-Slice Spiral CT Scans of the Heart", Aug. 2000.

* cited by examiner

*Primary Examiner*—David V. Bruce
*Assistant Examiner*—Hoon Song
(74) *Attorney, Agent, or Firm*—Oblon, Spivak, McClelland, Maier & Neustadt, P.C.

(57) ABSTRACT

An X-ray computed tomographic apparatus which employs both helical scan and segment reconstruction, specifies the temporal resolution of image data from a set helical pitch, a set rotational speed, and the heart rate of a patient, and then displays the specified temporal resolution on a scan plan screen.

19 Claims, 10 Drawing Sheets

| No. | SCAN MODE | START POSITION | END POSITION | CTDI (rGy) | kV | mA | ROTATIONAL SPEED | NUMBER OF SLICES | HELICAL PITCH | RECONSTRUCTION MODE |
|---|---|---|---|---|---|---|---|---|---|---|
| | | | | | MAIN | | RECONSTRUCTION CONDITIONS | WINDOW CONDITIONS | | |
| 1 | HELICAL | 015.00 | 075.00 | 20 | 100 | 150 | 0.4 | 4 | 4.0 | ECG GATED, HALF SEGMENT (3) |

PATIENT INFORMATION

GANTRY INFORMATION

SCANOGRAM IMAGE

COPY | CLEAR | BACK | TEMPORAL RESOLUTION (SIMPLE) | TEMPORAL RESOLUTION (REFINED) | VALIDATE

FIG. 10

X-RAY COMPUTED TOMOGRAPHIC APPARATUS

CROSS-REFERENCE TO RELATED APPLICATION

This application is based upon and claims the benefit of priority from the prior Japanese Patent Application No. 2003-070938, filed Mar. 14, 2003, the entire contents of which are incorporated herein by reference.

BACKGROUND OF THE INVENTION

1. Field of the Invention

The present invention relates to an X-ray computed tomographic apparatus which scans a patient by helical scan, and which reconstructs image data by ECG gated reconstruction on the basis of obtained data.

2. Description of the Related Art

An X-ray computed tomographic apparatus offers information about a patient, in terms of an image on the basis of the intensities of X-rays transmitted through a patient. It plays important roles in a large number of medical actions including the diagnoses and medical treatments of diseases, operation plans, etc.

Especially in the examination of the heart of fast motion as uses the X-ray computed tomographic apparatus, it is one of important problems to enhance the temporal resolution of an image. A major countermeasure against the problem is to shorten a time period per revolution of an X-ray tube, that is, to heighten the rotational speed of the X-ray tube. The rotational speed is also called "gantry speed" or "scan speed".

Figure 9:
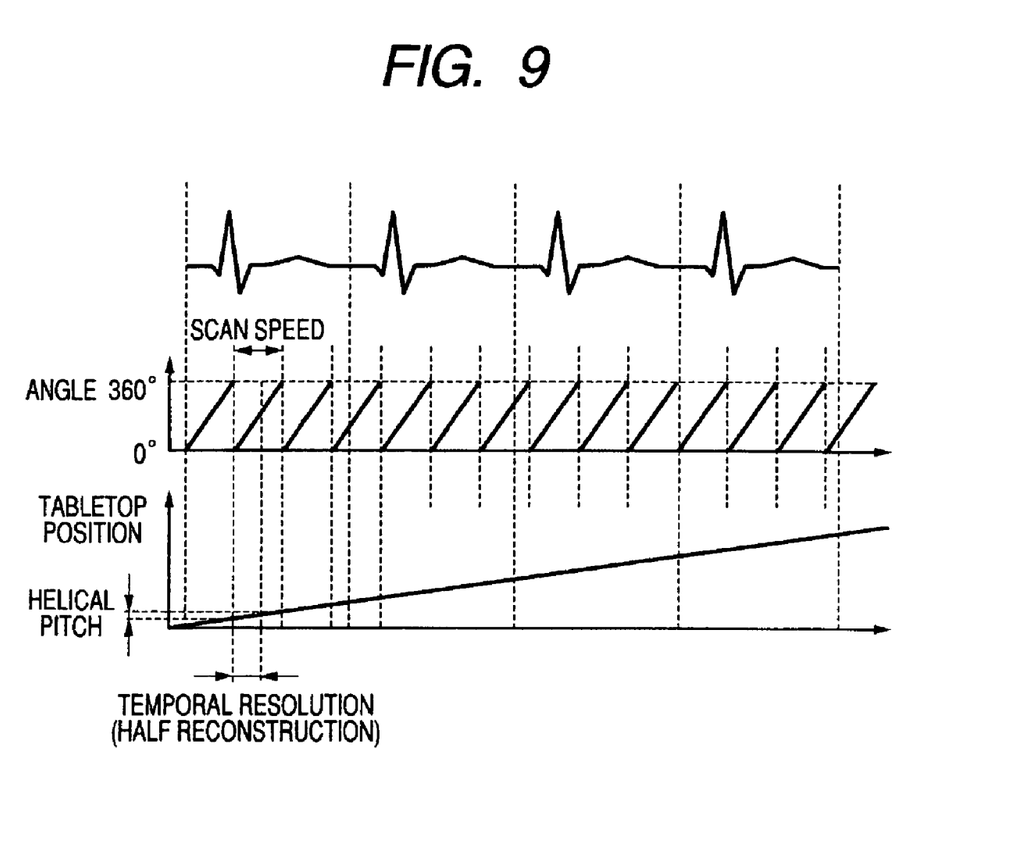
FIG. 9 is a diagram for explaining half reconstruction in the prior art.

A technique which can realize a temporal resolution higher than a rotational speed, is half reconstruction. As is well known, the half reconstruction reconstructs image data by the acquisition of projection data and the supplementation of the opposite data, the projection data being acquired while, as shown in FIG. 9, an X-ray tube rotates in a range of $180°+\alpha$ (where $\alpha$ denotes a fan angle) around the specified phase of the motion of the heart as designated by an operator, usually a position which is expressed in percent with 100 being the cardiac period of an electrocardiogram from a P wave to the next P wave. With the half reconstruction, a time period which is required for the X-ray tube to rotate in the range of $180°+\alpha$ is recognized as the temporal resolution of the image data.

Figure 10:
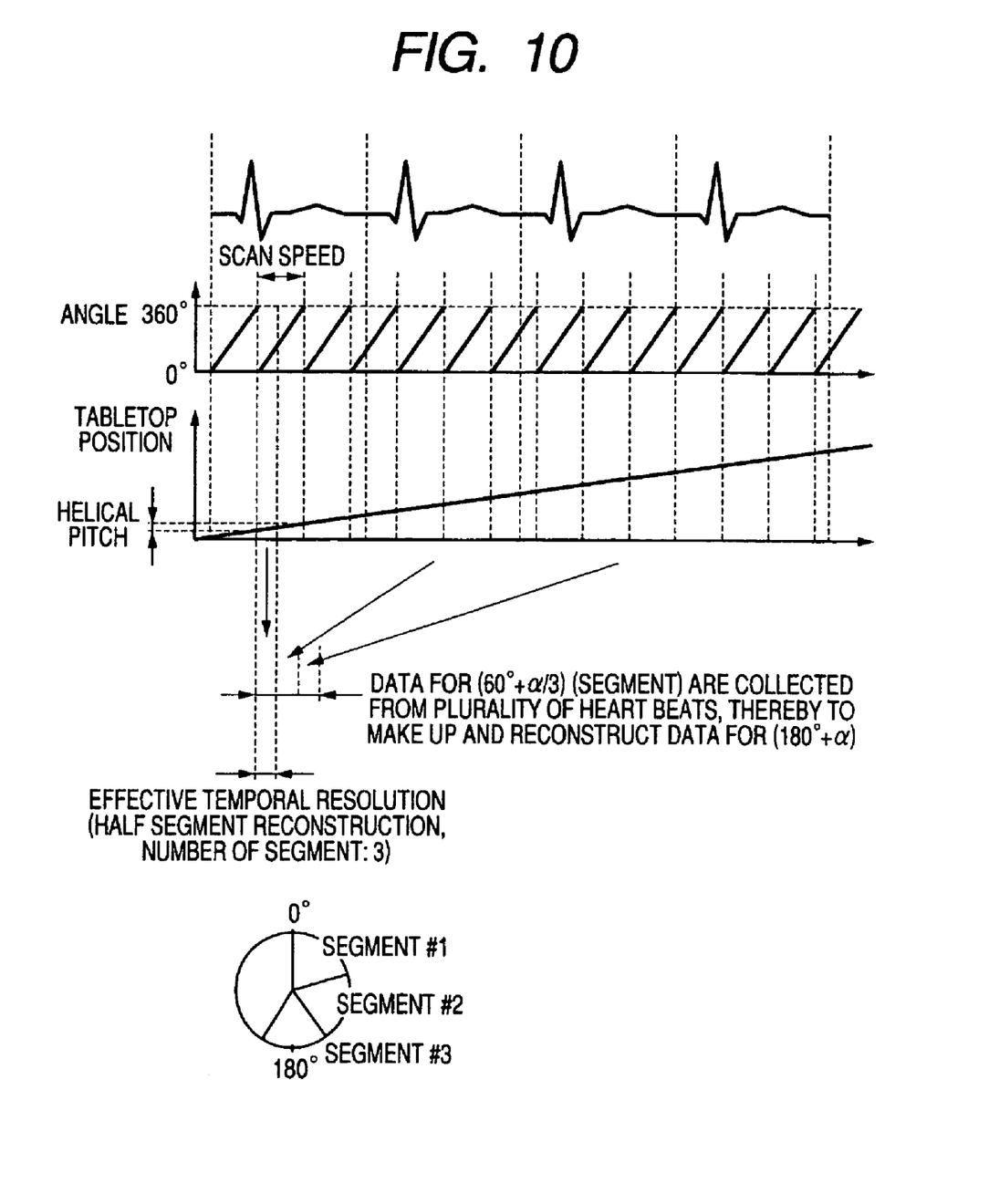
FIG. 10 is a diagram for explaining segment reconstruction in the prior art.

A technique which enhances the temporal resolution of an image more than the half reconstruction is segment reconstruction (also termed "ECG gated reconstruction"). The segment reconstruction the number of segments of which is 3 as shown in FIG. 10, features that projection data in ranges of $60°+\alpha/3$ are collected from within three continuous or discrete heart beats, thereby to make up projection data in the range of $180°+\alpha$. The ideal temporal resolution of the segment reconstruction is given as a time period which is required for an X-ray tube to rotate in the range of $60°+\alpha/3$.

The ideal temporal resolution is a temporal resolution under a specified situation in which the rotational period of the X-ray tube ideally shifts relatively to a cardiac period. In most cases where the shifts of the rotational period of the X-ray tube relative to the cardiac period are not ideal, temporal resolutions lower in accordance with the shifts of the rotational period of the X-ray tube relative to the cardiac period. The worst case takes place when the rotational period of the X-ray tube and the cardiac period have synchronized completely. In that case, the number of segments automatically becomes one, that is, the segment reconstruction completely veers to the half reconstruction, and the temporal resolution agrees with that in the half reconstruction.

In this manner, in the segment reconstruction, the temporal resolution fluctuates in accordance with the shift of the rotational period of the X-ray tube relative to the cardiac period, and hence, it is difficult to be intuitively grasped. In a case where helical scan is employed conjointly with the segment reconstruction, restrictions concerning an effective slice thickness are imposed, so that the temporal resolution is difficult to be grasped.

BRIEF SUMMARY OF THE INVENTION

An object of the present invention is to make scan conditions settable in consideration of the temporal resolution of a practical image corresponding to the heart rate of a patient, in an X-ray computed tomographic apparatus wherein image data are reconstructed under ECG gated reconstruction from data acquired by helical scan.

In the first aspect of the invention, an X-ray computed tomographic apparatus wherein image data are reconstructed on the basis of a plurality of data segments which extend over a plurality of heart beats extracted from data obtained by scanning a patient with X-rays under helical scan, comprises a setting device which is configured to set a helical pitch and a rotational speed concerning the helical scan; a temporal resolution data generation device which is configured to generate a temporal resolution of the image data that correspond to the set helical pitch, the set rotational speed, and a heart rate of the patient; a screen building device which is configured to build a scan plan screen that contains the set helical pitch, the set rotational speed, and the generated temporal resolution; and a display device which displays the scan plan screen.

In the second aspect of the invention, an X-ray computed tomographic apparatus wherein image data are reconstructed on the basis of a plurality of data segments which extend over a plurality of heart beats extracted from data obtained by scanning a patient with X-rays under helical scan, comprises a selection device which is configured to select a combination in which a temporal resolution of the image data corresponding to a heart rate of the patient becomes the shortest, from among a plurality of combinations of helical pitches and rotational speeds concerning the helical scan as satisfy an upper limit of a scan time; a screen building device which is configured to build a scan plan screen that contains the selected combination of the helical pitch and the rotational speed, and the shortest temporal resolution; and a display device which displays the scan plan screen.

In the third aspect of the invention, an X-ray computed tomographic apparatus wherein image data are reconstructed on the basis of a plurality of data segments which extend over a plurality of heart beats extracted from data obtained by scanning a patient with X-rays under helical scan, comprises a generation device which is configured to generate on the basis of a heart rate of the patient, a plurality of temporal resolutions which correspond respectively to a plurality of combinations of helical pitches and rotational speeds concerning the helical scan as satisfy an upper limit of a scan time; a screen building device which is configured to build a scan plan screen that contains the plurality of combinations of the helical pitches and the rotational speeds, and the plurality of generated temporal resolution; and a display device which displays the scan plan screen.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Now, an embodiment of an X-ray computed tomographic apparatus according to the present invention will be described with reference to the drawings. Incidentally, the X-ray computed tomographic apparatus includes various types such as the ROTATE/ROTATE type wherein an X-ray tube and a radiation detector rotate around a patient unitarily, and the STATIONARY/ROTATE type wherein a large number of detection elements are arrayed in the shape of a ring and wherein only an X-ray tube rotates around a patient. In this regard, the invention is applicable to any of the types. Here, the X-ray computed tomographic apparatus shall be described as the ROTATE/ROTATE type which holds the mainstream currently. Besides, projection data corresponding to one revolution around a patient are required for reconstructing the tomographic image data of one slice, and projection data corresponding to (180°+view angle) are required even in a half scan method. In this regard, the invention is applicable to either of the reconstruction schemes. Here, the half scan method will be taken as an example. In addition, the mainstreams of a mechanism for converting incident X-rays into charges are the indirect conversion type in which the X-rays are converted into light by the phosphor of a scintillator or the like and in which the light is further converted into the charges by a photoelectric element such as photodiode, and the direct conversion type which utilizes the creation of electron-hole pairs in a semiconductor based on the X-rays and the migrations of electrons and holes to electrodes, that is, a photoconductive phenomenon. Although either of the types may be adopted for an X-ray detection element, the indirect conversion type of the former will be referred to here. Further, in recent years, an X-ray computed tomographic apparatus of so-called "multiple tube type" wherein a plurality of pairs of X-ray tubes and X-ray detectors are mounted on a rotary ring has been brought into products, and the peripheral techniques thereof have been developed. The invention is applicable to either of a conventional X-ray computed tomographic apparatus of single tube type, and the X-ray computed tomographic apparatus of the multiple tube type. Here, the X-ray computed tomographic apparatus will be described as the single tube type.

Figure 1:
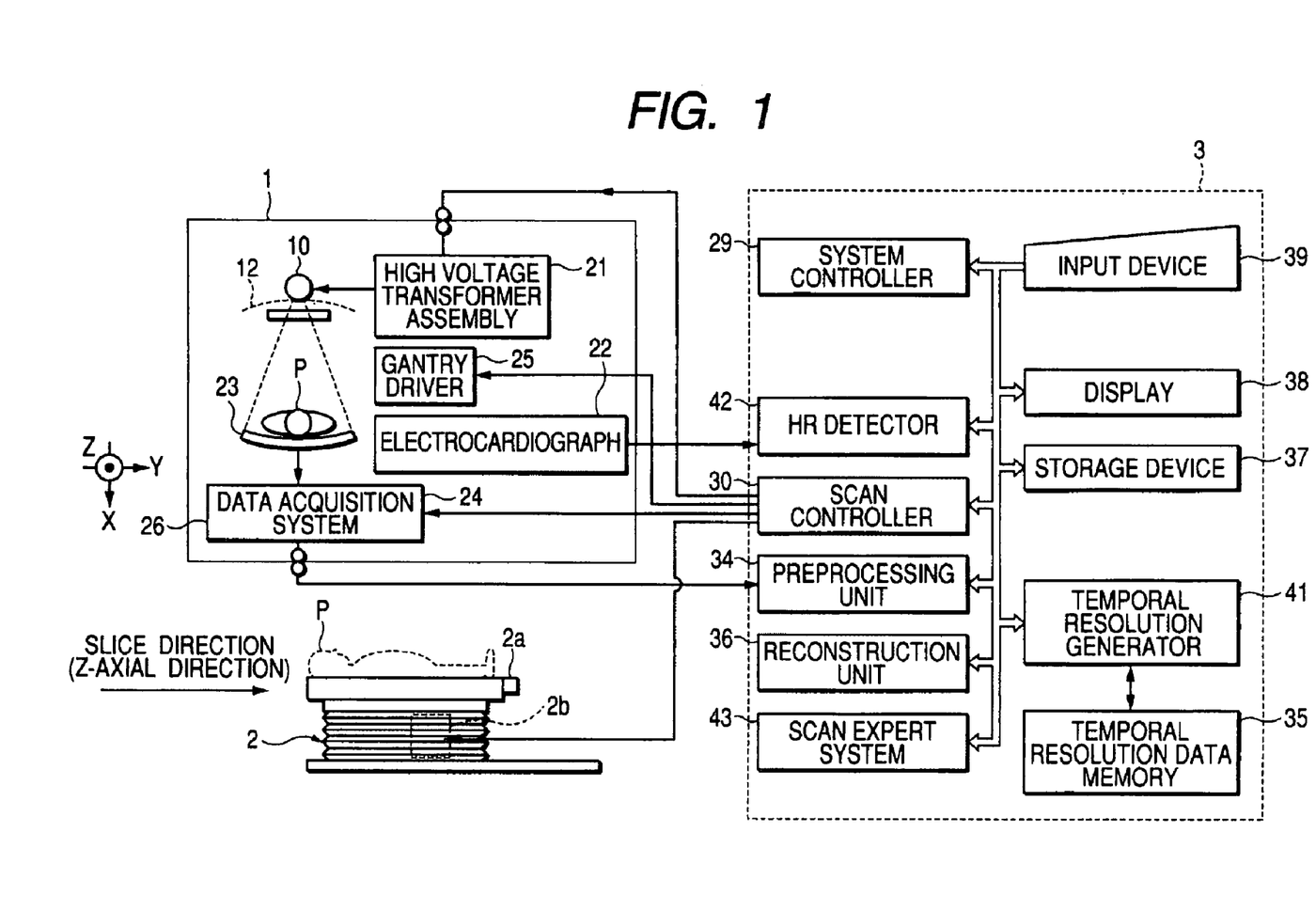
FIG. 1 is a diagram showing the layout of an X-ray computed tomographic apparatus according to an embodiment of the present invention.

FIG. 1 shows the configuration of the X-ray computed tomographic apparatus according to this embodiment. The X-ray computed tomographic apparatus includes a gantry 1 which is configured to acquire projection data about a patient. The gantry 1 includes an X-ray tube 10, and a multi-slice type X-ray detector 23. The X-ray tube 10 and the multi-slice type X-ray detector 23 are mounted on a ring-shaped rotary frame 12 which is driven and rotated by a gantry driver 25. The central part of the rotary frame 12 is opened, and the patient P placed on the tabletop 2a of a diagnostic table 2 is inserted into the opening. An electrocardiograph 22 is attached to the patient P in order to detect the electrocardiogram of the patient P.

A tube voltage is applied across the cathode and anode of the X-ray tube 10 by a high voltage transformer assembly 21, and filament current is fed to the filament of the X-ray tube 10 by the high voltage transformer assembly 21. X-rays are generated by the application of the tube voltage and the feed of the filament current.

Figure 2:
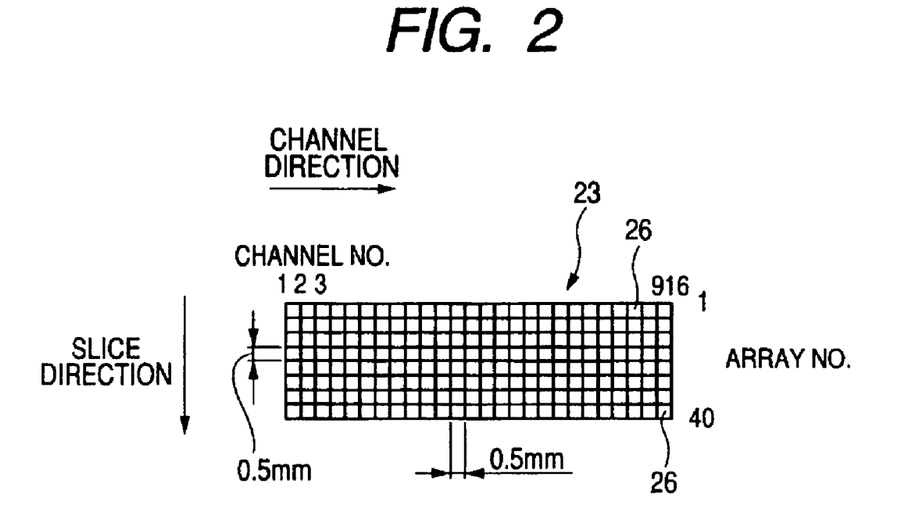
FIG. 2 is a plan view of an X-ray detector in FIG. 1.

As shown in FIG. 2, the multi-slice type X-ray detector 23 includes a plurality of X-ray detection elements 26 each of which has a square photocathode of, for example, 0.5 mm×0.5 mm. The X-ray detection elements 26 numbering, for example, 916 are arrayed in a channel direction. Such arrays numbering, for example, 40 are juxtaposed in a slice direction.

A data acquisition system 26 which is generally called "DAS", converts a signal outputted every channel from the detector 23, into a voltage signal, amplifies the voltage signal, and further converts the amplified signal into a digital signal. The data (raw data) here are supplied to a computer unit 3 disposed outside the gantry 1.

The preprocessing unit 34 of the computer unit 3 subjects the data (raw data) outputted from the data acquisition system 26, to correction processes such as sensitivity corrections, thereby to output projection data. The projection data are sent to the storage device 37 of the computer system 3, and are stored therein together with the electrocardiogram data of the electrocardiograph 22.

The computer system 3 is configured of the preprocessing unit 34 and storage device 37 mentioned above, and a system controller 29, an input device 39, a display device 38, a scan controller 30, a reconstruction unit 36, a scan expert system 43, a heart rate detector 42, a temporal resolution data memory 35 and a temporal resolution generator 41. The reconstruction unit 36 is adapted for both a half reconstruction process and a segment reconstruction process. The heart rate detector 42 has the function of identifying, for example, a P wave period from the electrocardiogram data, and then measuring the heart rate of the patient P on the basis of the identified period.

The temporal resolution generator 41 has the function of accessing the temporal resolution data memory 35 in compliance with the request of the scan expert system 43. By way of example, when the scan expert system 43 has issued the request for offering a temporal resolution, together with data about a rotational speed, a helical pitch and a heart rate, the temporal resolution generator 41 specifies the temporal resolution corresponding to the rotational speed, helical pitch and heart rate, and it sends the specified temporal resolution back to the scan expert system 43.

Figure 3:
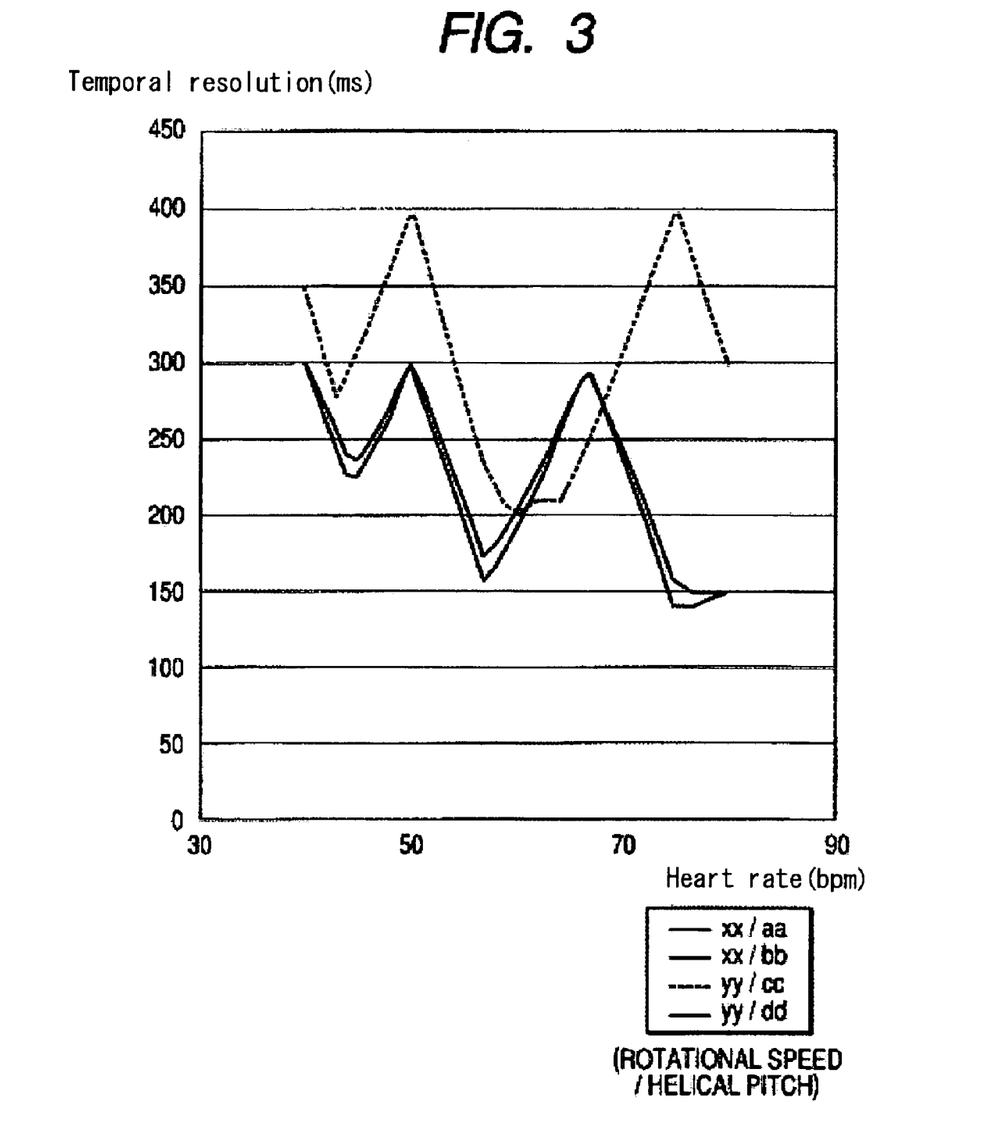
FIG. 3 is a diagram showing examples of temporal resolution profiles which are held in a temporal resolution data memory in FIG. 1.

The temporal resolution data memory 35 holds therein data about a plurality of temporal resolution profiles which have been obtained by computations or simulations on the basis of rotational speeds and helical pitches beforehand. FIG. 3 shows examples of four sorts of temporal resolution profiles conforming to the segment reconstruction. The four sorts of temporal resolution profiles correspond to four sorts of combinations of rotational speeds and helical pitches, respectively. The first combination is such that the rotational speed is xx (sec), while the helical pitch is aa (mm). The second combination is such that the rotational speed is xx (sec), while the helical pitch is bb (mm). The third combination is such that the rotational speed is yy (sec), while the helical pitch is cc (mm). The fourth combination is such that the rotational speed is yy (sec), while the helical pitch is dd (mm).

The temporal resolution profile expresses the change of the temporal resolution versus the change of the heart rate. The temporal resolution indicates an effective temporal resolution which is peculiar to the image data reconstructed by the half reconstruction or segment reconstruction process. With the half reconstruction process, the temporal resolution is simply given by a time period which is obtained in such a way that the rotational speed expressive of a time period required for one revolution of the X-ray tube 10 is multiplied by $(180°+\alpha)/360°$. On the other hand, with the segment reconstruction process, the temporal resolution is determined depending upon the rotational speed and helical pitch included in scan conditions, and also the heart rate of the patient P.

Incidentally, the helical pitch is defined as an actual distance which the tabletop 2a moves during one revolution of the X-ray tube 10, or as an index which is obtained by dividing the distance by a detector width in the slice direction, and the former will be exemplified here. The "detector width" is given by a length which is obtained in such a way that the number of all the arrays of the detector 23, or the number of arrays for use as designated by the operator is multiplied by the distance between the center lines of the adjacent arrays.

Data about the plurality of temporal resolution profiles which have the different combinations of rotational speeds and helical pitches, are prestored in the temporal resolution data memory 35, such as a ROM. The temporal resolution data memory 35 is so designed that the temporal resolution profile data can be read out therefrom, that data about a corresponding temporal resolution can be read out therefrom by receiving the rotational speed, helical pitch and heart rate, and that data about a corresponding rotational speed, helical pitch and temporal resolution can be read out therefrom by receiving the heart rate.

The scan expert system 43 is disposed in order to assist the operator in the job of determining a scan plan. It functions to determine the recommended values of scan conditions such as a reconstruction mode, a helical pitch (HP) and a scan or rotational speed (SS), and it builds a scan plan screen which contains the determined recommended values of the scan conditions, a temporal resolution, and a partial temporal resolution profile.

Figure 4:
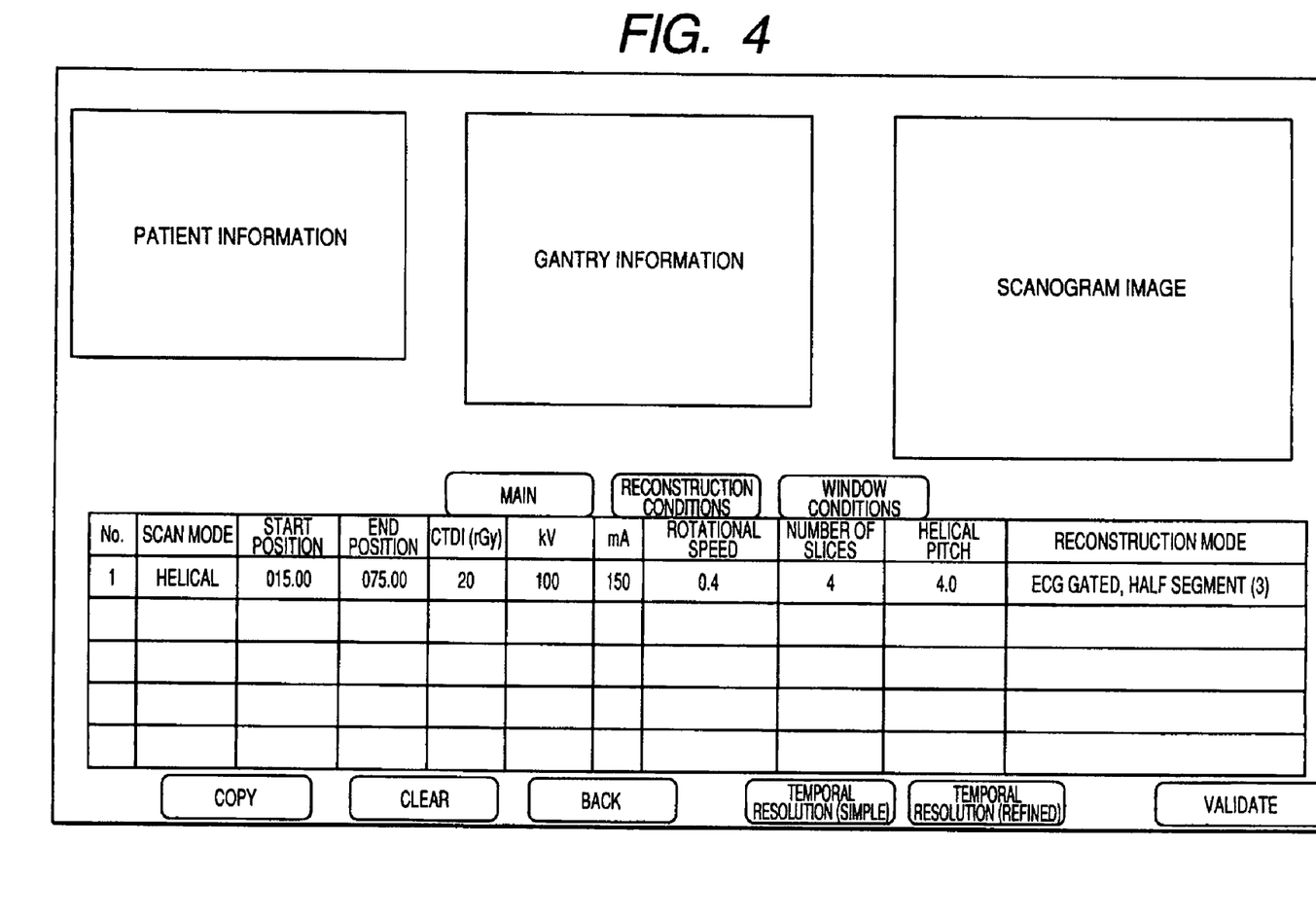
FIG. 4 is a diagram showing an example of a scan plan screen which is built by an expert system in FIG. 1.

FIG. 4 shows an example of the scan plan screen which is initially built by the scan expert system 43. Displayed on the scan plan screen are patient information, gantry information and a scanogram image, and also a part to-be-scanned designated or selected by the operator, and scan conditions, reconstruction conditions and window conditions planned by the scan expert system 43 in accordance with an examination plan. Contained as the scan conditions are, for example, a scan mode, a scan start position, a scan end position, "CTDI" (CT Dose Index) expressive of an exposed dose as stipulated by the Food and Drug Administration of the United States, a tube voltage "kV", a tube current "mA", a rotational speed, the number of slices (the number of arrays for use), a helical pitch, and a reconstruction mode. Besides, a button represented as "Temporal resolution (Simple)", and a button represented as "Temporal resolution (Refined)" are arranged on the scan plan screen.

When the operator has clicked the button represented as "Temporal resolution (Simple)", the scan expert system 43 activates a function for presenting a temporal resolution simply. The scan expert system 43 sends the temporal resolution generator 41 data about a helical pitch and a rotational speed which are planned, and the heart rate of the patient P as detected immediately before the planning, thereby to make a request for a temporal resolution corresponding to them. In compliance with the request, the temporal resolution generator 41 accesses the temporal resolution data memory 35 in accordance with the sent helical pitch, rotational speed and heart rate, thereby to obtain the temporal resolution corresponding to the helical pitch, rotational speed and heart rate, whereupon the temporal resolution generator 41 sends the obtained temporal resolution back to the scan expert system 43.

Figure 5:
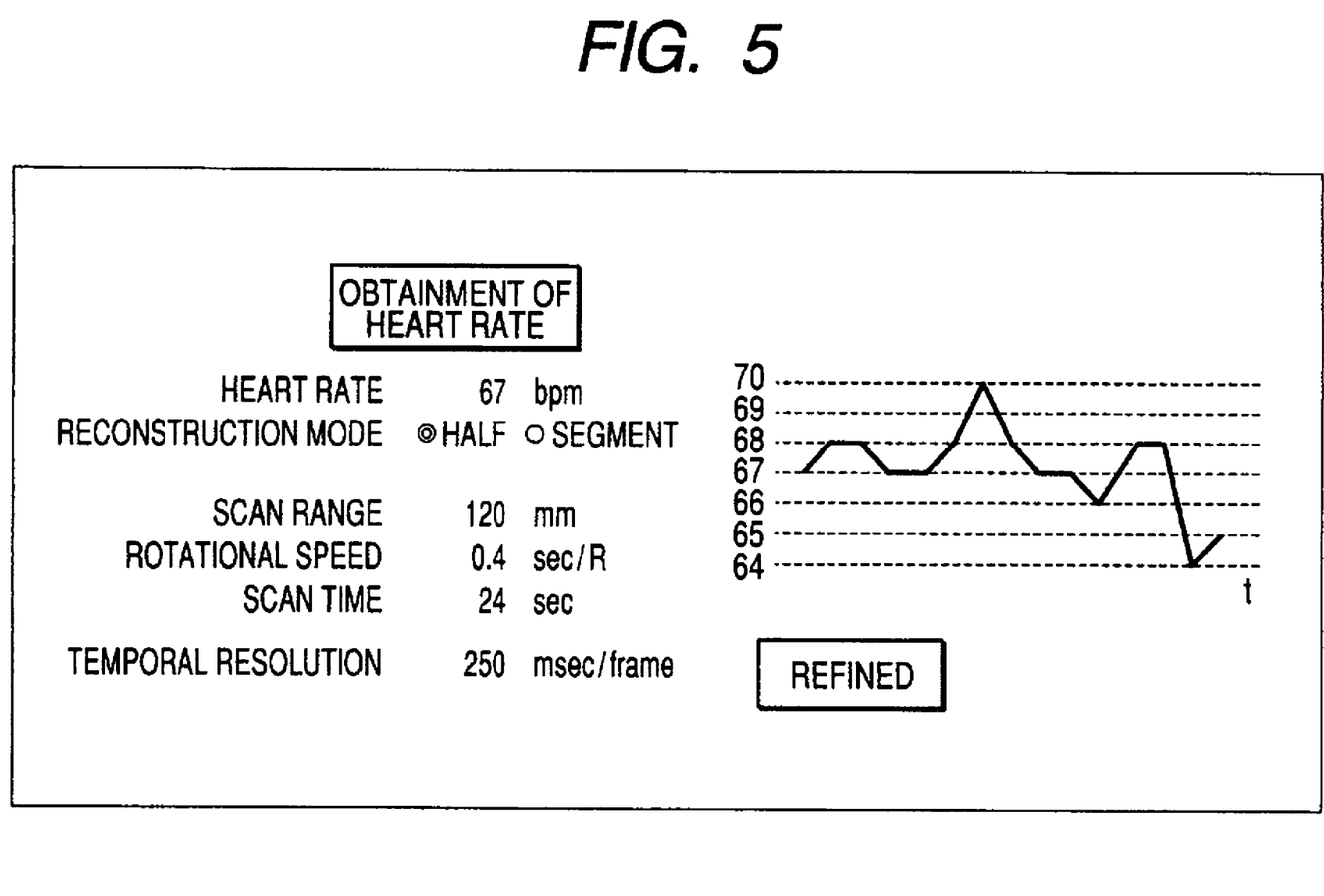
FIG. 5 is a diagram showing an example of a simple temporal resolution window which is popped up by clicking a "Temporal resolution (Simple)" button in FIG. 4.

The scan expert system 43 builds a scan plan screen (here, called "window" in order to distinguish this screen from FIG. 4) concerning the simple temporal resolution as shown in FIG. 5. More specifically, the window contains the helical pitch, rotational speed and heart rate, the temporal resolution corresponding to them as obtained from the temporal resolution generator 41, and a reconstruction mode. This window is displayed on the scan plan screen of FIG. 4 in a pop-up fashion. A button represented as "Obtainment of Heart rate", and a button represented as "Refined" are included in the window.

When the "Obtainment of Heart rate" button has been clicked, the scan expert system 43 request the heart rate detector 42 to offer data about the heart rate of the patient P. In compliance with the request, the heart rate detector 42 activates the electrocardiograph 22 and obtains the electrocardiogram data of the patient P for a predetermined time period, for example, 5 seconds. The heart rate detector 42 identifies characteristic waves, for example, P waves from the electrocardiogram data, and it computes the heart rate from the temporal width between the P waves, that is, a cardiac period every P wave. Thereafter, it supplies the computed heart rate as the data about the heart rate, to the scan expert system 43.

In actuality, the heart rate of the patient P is not constant, but it fluctuates. In the scan expert system 43, a mean heart rate (or median) is detected from the heart rates each of which is computed as a discrete value every P wave within the period of 5 seconds. The scan expert system 43 sends the temporal resolution generator 41 the detected mean hear rate together with the data about the planned helical pitch and rotational speed, and thus requests this generator 41 to offer a corresponding temporal resolution. The temporal resolution generator 41 obtains the temporal resolution corresponding to the mean heart rate and the planned helical pitch and rotational speed, from the temporal resolution data memory 35, and it sends the obtained temporal resolution back to the scan expert system 43.

The scan expert system 43 builds a scan plan screen (here, called "window" in order to distinguish this screen from FIG. 4) which contains the planned helical pitch and rotational speed, the mean heart rate, the temporal resolution corresponding to them as received from the temporal resolution generator 41, the reconstruction mode, and a graph expressing the temporal change of the heart rate. This window is displayed on the scan plan screen of FIG. 4 in a pop-up fashion.

Figure 6:
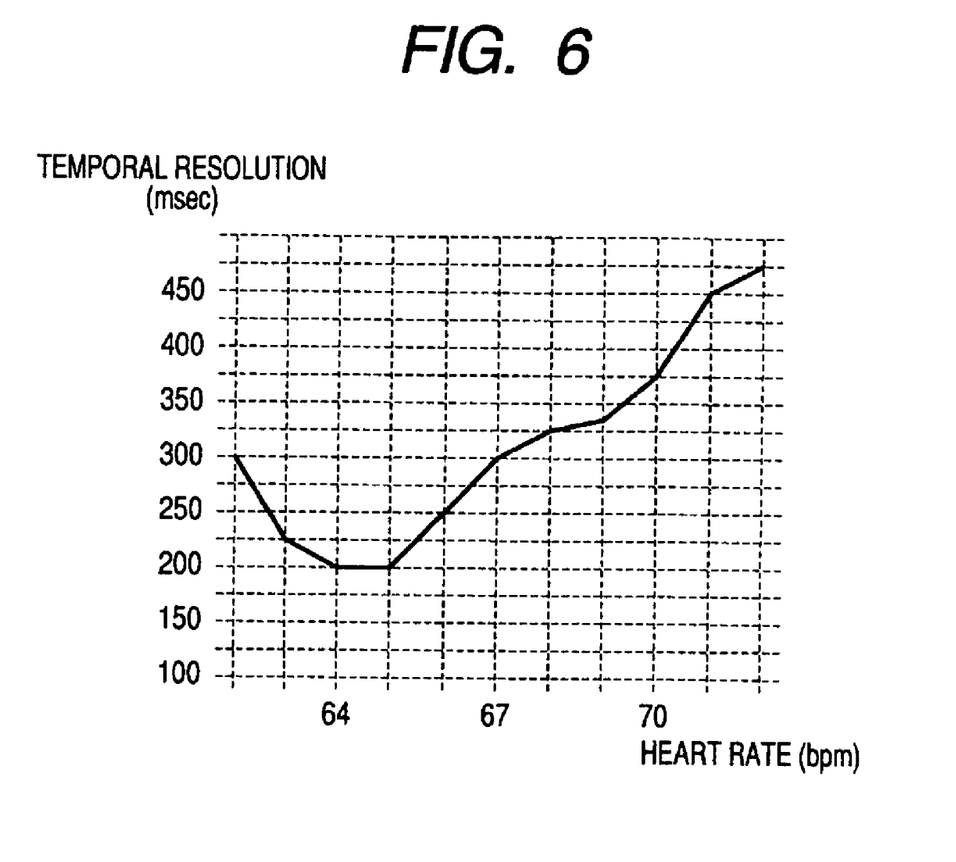
FIG. 6 is a diagram showing an example of a temporal resolution graph window which is popped up by clicking a "Refined" button in FIG. 5.

Subsequently, when the button represented as "Refined" has been clicked, the scan expert system 43 requests the temporal resolution generator 41 to offer the data of a temporal resolution profile corresponding to the planned helical pitch and rotational speed. The temporal resolution generator 41 reads out the data of the temporal resolution profile corresponding to the planned helical pitch and rotational speed, from the memory 35, and it sends the read-out data back to the scan expert system 43. The scan expert system 43 cuts out a partial temporal resolution profile of predetermined width centering round the mean heart rate, from the received temporal resolution profile, thereby to build a window shown in FIG. 6. In the example of FIG. 6, the partial temporal resolution profile is generated centering round the mean heart rate of 67 and having the width of 5 heart beats on each of both the sides of the central heart rate. This window contains the partial temporal resolution profile of the predetermined width centering round the mean heart rate.

As an actual job, the operator confirms the current planned helical pitch and rotational speed, and the temporal resolution corresponding to the mean heart rate of the patient P, in terms of numerical values and the profile, respectively. In a case where the confirmed temporal resolution is lower as compared with a desired temporal resolution, or where the former is excessively higher as compared with the latter, the operator goes back to the scan condition setting screen of FIG. 4 and alters at least either of the helical pitch and the rotational speed. After the alteration, the operator clicks the "Temporal resolution (Simple)" button and further clicks the "Obtainment of Heart rate" button and the "Refined" button as may be needed, whereby he/she can confirm a temporal resolution updated in correspondence with the altered helical pitch and rotational speed, on the window of FIG. 5 or FIG. 6. The operator can set the helical pitch and the rotational speed which can realize the desired temporal resolution, by repeating such jobs.

Referring back to FIG. 4, when the "Temporal resolution (Refined)" button on the scan condition setting screen has been clicked, the scan expert system 43 first requests the heart rate detector 42 to offer data about the heart rate of the patient P. In compliance with the request, the hear rate detector 42 activates the electrocardiograph 22 so as to obtain the electrocardiogram data of the patient P over a predetermined time period which is the longest breath-hold time, for example, 30 seconds designated for the patient P to-be-examined by the operator. A breath hold for the period of 30 seconds for obtaining the electrocardiogram data is required of the patient P as in an actual scan.

The longest breath-hold time is set as the upper limit of the scan time of helical scan. The heart rate detector 42 discretely computes a heart rate from the electrocardiogram data every P wave, and supplies data about such heart rates to the scan expert system 43. Then, the scan expert system 43 detects the lowest heart rate, highest heart rate and mean heart rate (or median) within 30 seconds, from the data about the heart rates.

The scan expert system 43 obtains partial temporal resolution profiles in a range from the detected lowest heart rate to the detected highest heart rate, concerning all the combinations of helical pitches and rotational speeds held in the memory 35, via the temporal resolution generator 41 or from the memory 35.

Figure 7:
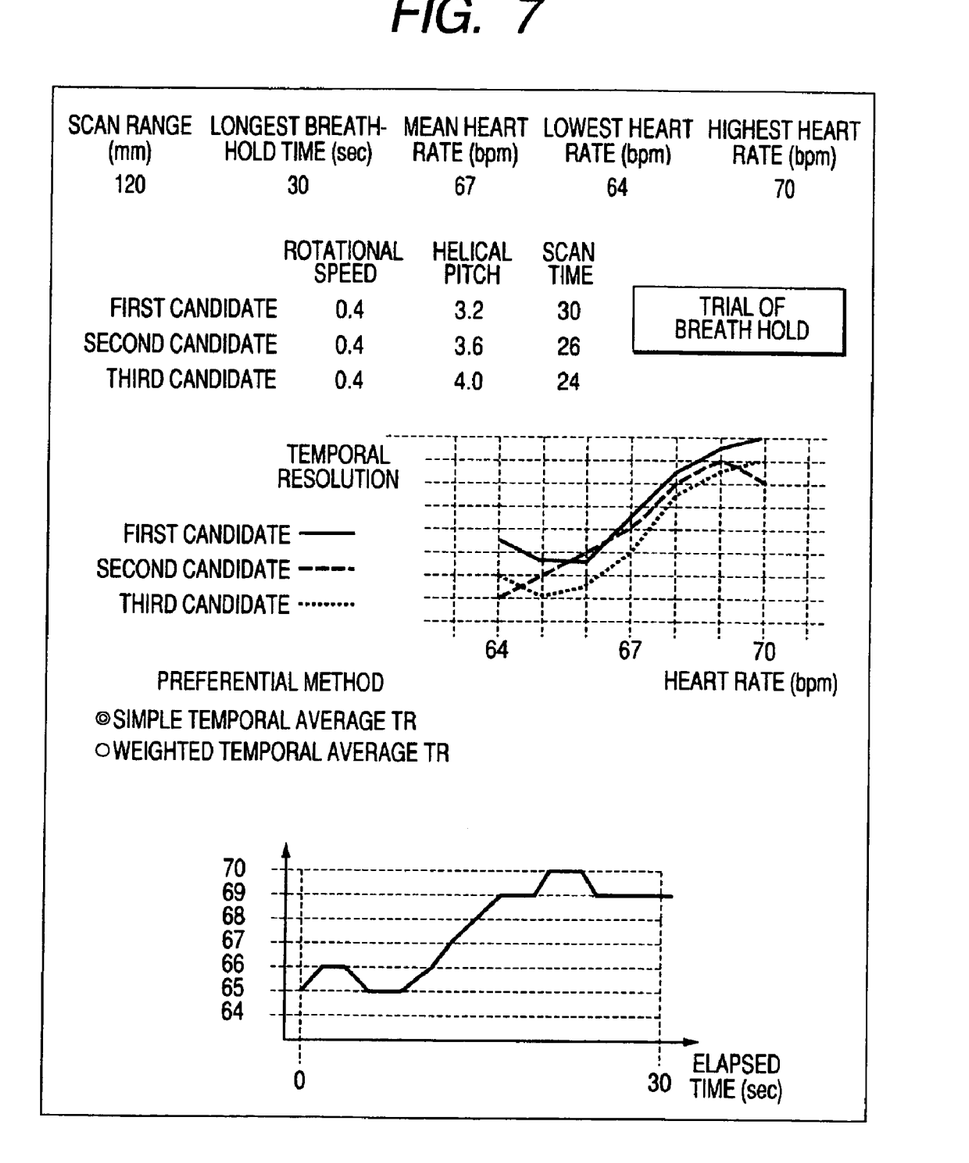
FIG. 7 is a diagram showing an example of a temporal resolution window which is popped up by clicking a "Temporal resolution (Refined)" button in FIG. 4.

Subsequently, the scan expert system 43 specifies a plurality of temporal resolutions to which the plurality of heart rates discretely obtained within 30 seconds correspond, every temporal resolution profile obtained, and it computes the temporal averages of the plurality of specified temporal resolutions. The operator can select the temporal averages of the temporal resolutions from between simple temporal averages and weighted temporal averages (refer to FIG. 7).

Besides, the scan expert system 43 selects from among the plurality of temporal resolution profiles, a predetermined number of temporal resolution profiles, here, three ones, as to which the computed temporal averages of the temporal resolutions are the shortest. Further, the scan expert system 43 builds a window exemplified in FIG. 7 as contains helical pitches and rotational speeds corresponding to the three selected temporal resolution profiles. In the window, the helical pitches and rotational speeds corresponding to the three selected temporal resolution profiles are offered together with scan times (also termed "radiographic times") each of which is obtained by dividing a scan range by the helical pitch, as first through third candidates in the order of higher temporal resolutions.

Incidentally, the scheme in which the plurality of candidates are presented and in which the operator is prompted to select any of them, may well be replaced with a scheme in which the scan expert system 43 automatically form a scan plan in the combination (helical pitch, rotational speed) that affords the shortest temporal average of the temporal resolution.

Also contained in the window are the graph of three partial temporal resolution profiles in which the longest breath-hold time, mean heart rate, lowest heart rate and highest heart rate lie within the limits of the lowest heart rate and highest heart rate cut out from the three selected temporal resolution profiles, and the graph of the temporal change of the measured heart rate. Upon confirming the respective temporal resolutions, the operator can select the desired plan from among the three candidates. If necessary, the job from the detection of the heart rate to the display of the window of FIG. 7 can be repeated any number of times, also for the patient's practice of the breath hold by clicking a button represented as "Trial of Breath hold".

Figure 8:
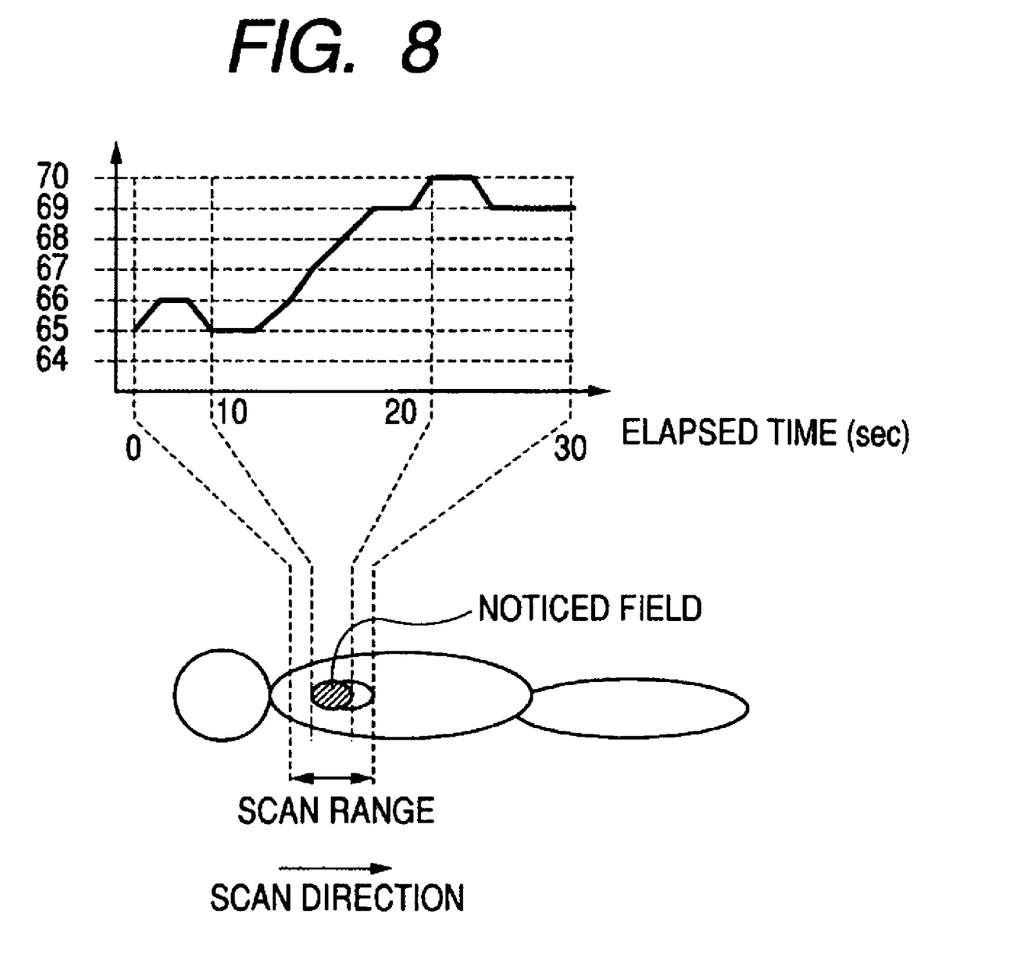
FIG. 8 is a diagram showing the temporal change of a heart rate in this embodiment.

The simple temporal averages of the temporal resolutions as mentioned above are obtained by simply averaging the plurality of heart rates which are discretely obtained at the respective P waves within the period of 30 seconds. The three candidates are selected from the temporal resolutions as to which the simple temporal averages are shorter. On the other hand, the weighted temporal averages of the temporal resolutions are obtained by weighting and averaging the plurality of heart rates which are discretely obtained at the respective P waves within the period of 30 seconds. As shown in FIG. 8 by way of example, the temporal resolution corresponding to the heart rate in the partial period of the period of 30 seconds is weighted more heavily than the temporal resolution corresponding to the heart rate in the other part. The partial period which is more heavily weighted is set at a period in which a noticed field in the scan range is scanned. By way of example, when the scan range is a chest range including the heart, the noticed field is set at an apical part. The desired temporal resolution can be realized in the noticed field by adopting the weighted temporal averages. Incidentally, the fluctuations of the heart rates during the breath-hold times are basically approximate between in prescan and actual scanning.

As described above, according to this embodiment, scan conditions, here, a rotational speed and a helical pitch can be set by confirming the temporal resolution of practical image data corresponding to the heart rate of a patient, and conversely, a rotational speed and a helical pitch as desired can be set from among candidates for rotational speeds and helical pitches of high temporal resolutions.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomographic apparatus wherein image data are reconstructed on the basis of a plurality of data segments which extend over a plurality of heart beats extracted from data obtained by scanning a patient with X-rays under helical scan, comprising:
    a setting device which is configured to set a helical pitch and a rotational speed concerning the helical scan;
    a temporal resolution data generation device which is configured to generate a temporal resolution of the image data that correspond to the set helical pitch, the set rotational speed, and a heart rate of the patient;
    a screen building device which is configured to build a scan-plan screen that contains the set helical pitch, the set rotational speed, and the generated temporal resolution; and
    a display device which displays the scan plan screen.

2. An X-ray computed tomographic apparatus as defined in claim 1, wherein the scan plan screen contains a graph which expresses a temporal change of the temporal resolution versus a temporal change of the heart rate of the patient.

3. An X-ray computed tomographic apparatus as defined in claim 1, wherein the scan plan screen contains a temporal change of the heart rate of the patient.

4. An X-ray computed tomographic apparatus as defined in claim 1, wherein the scan plan screen contains a button for obtaining the heart rate of the patient.

5. An X-ray computed tomographic apparatus as defined in claim 1, wherein the scan plan screen contains a box for inputting the heart rate of the patient.

6. An X-ray computed tomographic apparatus as defined in claim 1, wherein the heart rate is a mean heart rate or a median within a predetermined period.

7. An X-ray computed tomographic apparatus wherein image data are reconstructed on the basis of a plurality of data segments which extend over a plurality of heart beats extracted from data obtained by scanning a patient with X-rays under helical scan, comprising:
    a selection device which is configured to select a combination in which a temporal resolution of the image data corresponding to a heart rate of the patient becomes the shortest, from among a plurality of combinations of helical pitches and rotational speeds concerning the helical scan as satisfy an upper limit of a scan time;
    a screen building device which is configured to build a scan plan screen that contains the selected combination of the helical pitch and the rotational speed, and the shortest temporal resolution; and
    a display device which displays the scan plan screen,
    wherein the scan plan screen contains a graph which expresses a temporal change of the temporal resolution versus a temporal chance of the heart rate of the patient.

8. An X-ray computed tomographic apparatus as defined in claim 7, wherein the scan plan screen contains a temporal change of the heart rate of the patient.

9. An X-ray computed tomographic apparatus as defined in claim 7, wherein the heart rate is a mean heart rate or a median within a predetermined period.

10. An X-ray computed tomographic apparatus as defined in claim 7, wherein the selection device selects from among the plurality of combinations, a combination in which a temporal average concerning a temporal change of the temporal resolution corresponding to a temporal change of the heart rate within a scheduled breath-hold time period becomes the shortest.

11. An X-ray computed tomographic apparatus as defined in claim 10, wherein the temporal average is a simple temporal average.

12. An X-ray computed tomographic apparatus as defined in claim 10, wherein the temporal average is a weighted temporal average.

13. An X-ray computed tomographic apparatus wherein image data are reconstructed on the basis of a plurality of data segments which extend over a plurality of heart beats extracted from data obtained by scanning a patient with X-rays under helical scan, comprising:
    a generation device which is configured to generate on the basis of a heart rate of the patient, a plurality of temporal resolutions which correspond respectively to a plurality of combinations of helical pitches and rotational speeds concerning the helical scan as satisfy an upper limit of a scan time;
    a screen building device which is configured to build a scan plan screen that contains the plurality of combinations of the helical pitches and the rotational speeds, and the plurality of generated temporal resolution; and
    a display device which displays the scan plan screen.

14. An X-ray computed tomographic apparatus as defined in claim 13, wherein the scan plan screen contains a graph which expresses a temporal change of the temporal resolution versus a temporal change of the heart rate of the patient.

15. An X-ray computed tomographic apparatus as defined in claim 13, wherein the scan plan screen contains a temporal change of the heart rate of the patient.

16. An X-ray computed tomographic apparatus as defined in claim 13, wherein the heart rate is a mean heart rate or a median within a predetermined period.

17. An X-ray computed tomographic apparatus as defined in claim 13, wherein the generation device generates a temporal average concerning a temporal change of the temporal resolution corresponding to a temporal change of the heart rate within a scheduled breath-hold time period.

18. An X-ray computed tomographic apparatus as defined-in-claim 17, wherein the temporal average is a simple temporal average.

19. An X-ray computed tomographic apparatus as defined in claim 17, wherein the temporal average is a weighted temporal average.

* * * * *